(12) United States Patent
Rossetto (10) Patent No.: US 8,282,632 B2
(45) Date of Patent: Oct. 9, 2012

(54) FEEDPOINT OPTIMIZATION FOR MICROWAVE ABLATION DIPOLE ANTENNA WITH INTEGRATED TIP

(75) Inventor: Francesca Rossetto, Longmont, CO (US)

(73) Assignee: Vivant Medical, Inc., Boulder, CO (US)

( * ) Notice: Subject to any disclaimer, the term of this patent is extended or adjusted under 35 U.S.C. 154(b) by 413 days.

(21) Appl. No.: 12/568,067

(22) Filed: Sep. 28, 2009

(65) Prior Publication Data

US 2011/0077632 A1 Mar. 31, 2011

(51) Int. Cl.
*A61B 18/18* (2006.01)
(52) U.S. Cl. .................... 606/33; 606/41; 607/156
(58) Field of Classification Search ............ 606/33–45; 607/101, 102, 156
See application file for complete search history.

(56) References Cited

U.S. PATENT DOCUMENTS

| | | | | |
|---|---|---|---|---|
| 5,275,597 | A | * | 1/1994 | Higgins et al. ............. 606/33 |
| 5,693,082 | A | * | 12/1997 | Warner et al. ............. 607/156 |
| 5,904,709 | A | | 5/1999 | Arndt et al. |
| 6,134,476 | A | | 10/2000 | Arndt et al. |
| 6,175,768 | B1 | | 1/2001 | Arndt et al. |
| 6,289,249 | B1 | | 9/2001 | Arndt et al. |
| 6,512,956 | B2 | | 1/2003 | Arndt et al. |
| 6,592,579 | B2 | | 7/2003 | Arndt et al. |
| 6,675,050 | B2 | | 1/2004 | Arndt et al. |
| 2003/0088242 | A1 | * | 5/2003 | Prakash et al. ............. 606/33 |

FOREIGN PATENT DOCUMENTS

| | | |
|---|---|---|
| DE | 390937 | 3/1924 |
| DE | 1099658 | 2/1961 |
| DE | 1139927 | 11/1962 |
| DE | 1149832 | 6/1963 |
| DE | 1439302 | 1/1969 |
| DE | 2439587 | 2/1975 |
| DE | 2455174 | 5/1975 |
| DE | 2407559 | 8/1975 |
| DE | 2415263 | 10/1975 |
| DE | 2429021 | 1/1976 |
| DE | 2460481 | 6/1976 |
| DE | 2602517 | 7/1976 |
| DE | 2504280 | 8/1976 |
| DE | 2627679 | 1/1977 |
| DE | 2540968 | 3/1977 |
| DE | 2820908 | 11/1978 |
| DE | 2803275 | 8/1979 |
| DE | 2823291 | 11/1979 |
| DE | 2946728 | 5/1981 |
| DE | 3143421 | 5/1982 |
| DE | 3045996 | 7/1982 |
| DE | 3120102 | 12/1982 |
| DE | 3510586 | 10/1986 |

(Continued)

OTHER PUBLICATIONS

U.S. Appl. No. 08/483,742, filed Jun. 7, 1995.

(Continued)

*Primary Examiner* — Linda Dvorak
*Assistant Examiner* — Amanda Scott (57) ABSTRACT

A microwave ablation system includes a generator operable to output energy and an antenna coupled to the generator via a coaxial cable. The antenna delivers energy to tissue and includes a proximal radiating section and a distal radiating section. The antenna also includes a feedpoint section defined by the portion of the distal radiating section that underlaps the proximal radiating section.

14 Claims, 2 Drawing Sheets

FOREIGN PATENT DOCUMENTS

| | | |
|---|---|---|
| DE | 3604823 | 8/1987 |
| DE | 8712328 | 3/1988 |
| DE | 3711511 | 6/1988 |
| DE | 3904558 | 8/1990 |
| DE | 3942998 | 7/1991 |
| DE | 4238263 | 5/1993 |
| DE | 4303882 | 8/1994 |
| DE | 4339049 | 5/1995 |
| DE | 29616210 | 1/1997 |
| DE | 19608716 | 4/1997 |
| DE | 19751106 | 5/1998 |
| DE | 19717411 | 11/1998 |
| DE | 19751108 | 5/1999 |
| DE | 19801173 | 7/1999 |
| DE | 19848540 | 5/2000 |
| DE | 10224154 | 12/2003 |
| DE | 10328514 | 3/2005 |
| DE | 102004022206 | 12/2005 |
| DE | 202005015147 | 3/2006 |
| EP | 0 246 350 | 11/1987 |
| EP | 0 521 264 | 1/1993 |
| EP | 0 556 705 | 8/1993 |
| EP | 0 558 429 | 9/1993 |
| EP | 0 836 868 | 4/1998 |
| EP | 1 159 926 | 5/2001 |
| FR | 179 607 | 11/1906 |
| FR | 1 275 415 | 9/1960 |
| FR | 1 347 865 | 11/1963 |
| FR | 2 276 027 | 6/1974 |
| FR | 2 235 669 | 1/1975 |
| FR | 2 313 708 | 12/1976 |
| FR | 2 502 935 | 10/1982 |
| FR | 2 517 953 | 6/1983 |
| FR | 2 573 301 | 11/1984 |
| FR | 2 862 813 | 5/2005 |
| FR | 2 864 439 | 7/2005 |
| JP | 5-5106 | 1/1993 |
| JP | 05-40112 | 2/1993 |
| JP | 06343644 | 12/1994 |
| JP | 07265328 | 10/1995 |
| JP | 08056955 | 3/1996 |
| JP | 08252263 | 10/1996 |
| JP | 09010223 | 1/1997 |
| JP | 11244298 | 9/1999 |
| JP | 2000342599 | 12/2000 |
| JP | 2000350732 | 12/2000 |
| JP | 2001008944 | 1/2001 |
| JP | 2001029356 | 2/2001 |
| JP | 2001128990 | 5/2001 |
| SU | 166452 | 11/1964 |
| SU | 401367 | 11/1974 |
| SU | 727201 | 4/1980 |

OTHER PUBLICATIONS

U.S. Appl. No. 08/136,098, filed Oct. 14, 1993.
U.S. Appl. No. 12/129,482, filed May 29, 2008.
U.S. Appl. No. 12/135,425, filed Jun. 9, 2008.
U.S. Appl. No. 12/135,690, filed Jun. 9, 2008.
U.S. Appl. No. 12/147,093, filed Jun. 26, 2008.
U.S. Appl. No. 12/181,504, filed Jul. 29, 2008.
U.S. Appl. No. 12/184,556, filed Aug. 1, 2008.
U.S. Appl. No. 12/194,254, filed Aug. 19, 2008.
U.S. Appl. No. 12/197,601, filed Aug. 25, 2008.
U.S. Appl. No. 12/197,405, filed Aug. 25, 2008.
U.S. Appl. No. 12/197,473, filed Aug. 25, 2008.
U.S. Appl. No. 12/199,935, filed Aug. 28, 2008.
U.S. Appl. No. 12/203,474, filed Sep. 3, 2008.
U.S. Appl. No. 12/236,686, filed Sep. 24, 2008.
U.S. Appl. No. 12/244,850, filed Oct. 3, 2008.
U.S. Appl. No. 12/250,110, filed Oct. 13, 2008.
U.S. Appl. No. 12/250,171, filed Oct. 13, 2008.
U.S. Appl. No. 12/251,857, filed Oct. 15, 2008.
U.S. Appl. No. 12/253,457, filed Oct. 17, 2008.
U.S. Appl. No. 12/366,298, filed Feb. 5, 2009.
U.S. Appl. No. 12/389,906, filed Feb. 20, 2009.
U.S. Appl. No. 12/389,915, filed Feb. 20, 2009.
U.S. Appl. No. 12/401,268, filed Mar. 10, 2009.
U.S. Appl. No. 12/416,583, filed Apr. 1, 2009.
U.S. Appl. No. 12/419,395, filed Apr. 7, 2009.
U.S. Appl. No. 12/423,609, filed Apr. 14, 2009.
U.S. Appl. No. 12/434,903, filed May 4, 2009.
U.S. Appl. No. 12/436,237, filed May 6, 2009.
U.S. Appl. No. 12/436,239, filed May 6, 2009.
U.S. Appl. No. 12/436,231, filed May 6, 2009.
U.S. Appl. No. 12/472,831, filed May 27, 2009.
U.S. Appl. No. 12/475,082, filed May 29, 2009.
U.S. Appl. No. 12/476,960, filed Jun. 2, 2009.
U.S. Appl. No. 12/487,917, filed Jun. 19, 2009.
U.S. Appl. No. 12/493,302, filed Jun. 29, 2009.
U.S. Appl. No. 12/504,738, filed Jul. 17, 2009.
U.S. Appl. No. 12/508,700, filed Jul. 24, 2009.
U.S. Appl. No. 12/535,851, filed Aug. 5, 2009.
U.S. Appl. No. 12/535,856, filed Aug. 5, 2009.
U.S. Appl. No. 12/536,616, filed Aug. 6, 2009.
U.S. Appl. No. 12/542,348, filed Aug. 17, 2009.
U.S. Appl. No. 12/542,785, filed Aug. 18, 2009.
U.S. Appl. No. 12/547,155, filed Aug. 25, 2009.
U.S. Appl. No. 12/548,644, filed Aug. 27, 2009.
U.S. Appl. No. 12/555,576, filed Sep. 8, 2009.
U.S. Appl. No. 12/556,010, filed Sep. 9, 2009.
U.S. Appl. No. 12/561,096, filed Sep. 16, 2009.
U.S. Appl. No. 12/562,575, filed Sep. 18, 2009.
U.S. Appl. No. 12/562,842, filed Sep. 18, 2009.
U.S. Appl. No. 12/566,299, filed Sep. 24, 2009.
U.S. Appl. No. 12/568,067, filed Sep. 28, 2009.
U.S. Appl. No. 12/568,524, filed Sep. 28, 2009.
U.S. Appl. No. 12/568,551, filed Sep. 28, 2009.
U.S. Appl. No. 12/568,777, filed Sep. 29, 2009.
U.S. Appl. No. 12/568,838, filed Sep. 29, 2009.
U.S. Appl. No. 12/568,883, filed Sep. 29, 2009.
U.S. Appl. No. 12/568,972, filed Sep. 29, 2009.
U.S. Appl. No. 12/569,171, filed Sep. 29, 2009.
U.S. Appl. No. 12/569,685, filed Sep. 29, 2009.
U.S. Appl. No. 12/582,857, filed Oct. 21, 2009.
U.S. Appl. No. 12/606,769, filed Oct. 27, 2009.
U.S. Appl. No. 12/607,221, filed Oct. 28, 2009.
U.S. Appl. No. 12/607,268, filed Oct. 28, 2009.
U.S. Appl. No. 12/619,462, filed Nov. 16, 2009.
U.S. Appl. No. 12/620,289, filed Nov. 17, 2009.
Alexander et al., "Magnetic Resonance Image-Directed Stereotactic Neurosurgery: Use of Image Fusion with Computerized Tomography to Enhance Spatial Accuracy" Journal Neurosurgery, 83 (1995), pp. 271-276.
Anderson et al., "A Numerical Study of Rapid Heating for High Temperature Radio Frequency Hyperthermia" International Journal of Bio-Medical Computing, 35 (1994), pp. 297-307.
Anonymous. (1999) Auto Suture MIBB Site Marker: Single Use Clip Applier, United States Surgical (Product instructions), 2 pages.
Anonymous. (2001) Disposable Chiba Biopsy Needles and Trays, Biopsy and Special Purpose Needles Cook Diagnostic and Interventional Products Catalog (products list), 4 pages.
Anonymous. (1987) Homer Mammalok™ Breast Lesion Needle/Wire Localizer, Namic ® Angiographic Systems Division, Glens Falls, New York, (Hospital products price list), 4 pages.
Anonymous. (1999) MIBB Site Marker, United States Surgical (Sales brochure), 4 pages.
Anonymous. Blunt Tubes with Finished Ends. Pointed Cannula, Popper & Sons Biomedical Instrument Division, (Products Price List), one page, Jul. 19, 2000.
Anonymous. Ground Cannulae, ISPG, New Milford, CT, (Advertisement) one page, Jul. 19, 2000.
B. Levy M.D. et al., "Randomized Trial of Suture Versus Electrosurgical Bipolar Vessel Sealing in Vaginal Hysterectomy" Obstetrics & Gynecology, vol. 102, No. 1, Jul. 2003.
B. Levy M.D. et al., "Update on Hysterectomy New Technologies and Techniques" OBG Management, Feb. 2003.
B. Levy M.D., "Use of a New Vessel Ligation Device During Vaginal Hysterectomy" FIGO 2000, Washington, D.C.

B. F. Mullan et al., (May 1999) "Lung Nodules: Improved Wire for CT-Guided Localization," Radiology 211:561-565.

B. T. Heniford M.D. et al., "Initial Research and Clinical Results with an Electrothermal Bipolar Vessel Sealer" Oct. 1999.

Bergdahl et al., "Studies on Coagulation and the Development of an Automatic Computerized Bipolar Coagulator" Journal of Neurosurgery 75:1 (Jul. 1991), pp. 148-151.

Bulletin of the American Physical Society, vol. 47, No. 5, Aug. 2002, p. 41.

C. F. Gottlieb et al., "Interstitial Microwave Hyperthermia Applicators having Submillimetre Diameters", Int. J. Hyperthermia, vol. 6, No. 3, pp. 707-714, 1990.

C. H. Durney et al., "Antennas for Medical Applications", Antenna Handbook: Theory Application and Design, p. 24-40, Van Nostrand Reinhold, 1988 New York, V.T. Lo, S.W. Lee.

Carbonell et al., "Comparison of the Gyrus PlasmaKinetic Sealer and the Valleylab LigaSure™ Device in the Hemostasis of Small, Medium, and Large-Sized Arteries" Carolinas Laparoscopic and Advanced Surgery Program, Carolinas Medical Center, Charlotte, NC 2003.

Carus et al., "Initial Experience With the LigaSure™ Vessel Sealing System in Abdominal Surgery" Innovations That Work, Jun. 2002.

Chicharo et al., "A Sliding Goertzel Algorithm" Aug. 1996 DOS pp. 283-297 Signal Processing, Elsevier Science Publishers B.V. Amsterdam, NL, vol. 52, No. 3.

Chou, C.K., (1995) "Radiofrequency Hyperthermia in Cancer Therapy," Chapter 94 In Biologic Effects of Nonionizing Electromagnetic Fields, CRC Press, Inc., pp. 1424-1428.

Chung et al., "Clinical Experience of Sutureless Closed Hemorrhoidectomy with LigaSure™" Diseases of the Colon & Rectum, vol. 46, No. 1, Jan. 2003.

Cosman et al., "Methods of Making Nervous System Lesions" in William RH, Rengachary SS (eds): Neurosurgery, New York: McGraw•Hill, vol. 111, (1984), pp. 2490-2499.

Cosman et al., "Radiofrequency Lesion Generation and its Effect on Tissue Impedence", Applied Neurophysiology, 51:230-242, 1988.

Cosman et al., "Theoretical Aspects of Radiofrequency Lesions in the Dorsal Root Entry Zone" Neurosurgery 15:(1984), pp. 945-950.

Crawford et al., "Use of the LigaSure™ Vessel Sealing System in Urologic Cancer Surger" Grand Rounds in Urology 1999, vol. 1, Issue 4, pp. 10-17.

Dulemba et al., "Use of a Bipolar Electrothermal Vessel Sealer in Laparoscopically Assisted Vaginal Hysterectomy" Sales/Product Literature; Jan. 2004.

E. David Crawford, "Evaluation of a New Vessel Sealing Device in Urologic Cancer Surgery" Sales/Product Literature 2000.

E. David Crawford, "Use of a Novel Vessel Sealing Technology in Management of the Dorsal Veinous Complex" Sales/Product Literature 2000.

Esterline, "Light Key Projection Keyboard" 2004 Advanced Input Systems, located at: <http://www.advanced-input.com/lightkey> last visited on Feb. 10, 2005.

Esterline Product Literature, "Light Key: Visualize a Virtual Keyboard. One With No Moving Parts", Nov. 1, 2003; 4 pages.

Geddes et al., "The Measurement of Physiologic Events by Electrical Impedence" Am. J. MI, Jan. Mar. 1964, pp. 16-27.

Goldberg et al., "Image-guided Radiofrequency Tumor Ablation: Challenges and Opportunities—Part I", (2001) J Vasc. Interv. Radiol, vol. 12, pp. 1021-1032.

Goldberg et al., "Tissue Ablation with Radiofrequency: Effect of Probe Size, Gauge, Duration, and Temperature on Lesion Volume" Acad Radio (1995) vol. 2, No. 5, pp. 399-404.

H. Schwarzmaier et al., "Magnetic Resonance Imaging of Microwave Induced Tissue Heating" Dept. of Laser Medicine & Dept. of Diagnostic Radiology; Heinrich-Heine-University, Duesseldorf, Germany; Dec. 8, 1994; pp. 729-731.

Heniford et al., "Initial Results with an Electrothermal Bipolar Vessel Sealer" Surgical Endoscopy (2001) 15:799-801.

Herman at al., "Laparoscopic Intestinal Resection With the LigaSure™ Vessel Sealing System: A Case Report" Innovations That Work, Feb. 2002.

Humphries Jr. et al., "Finite•Element Codes to Model Electrical Heating and Non•LInear Thermal Transport in Biological Media", Proc. ASME HTD-355, 131 (1997).

Ian D. McRury et al., The Effect of Ablation Sequence and Duration on Lesion Shape Using Rapidly Pulsed Radiofrequency Energy Through Electrodes, Feb. 2000, Springer Netherlands, vol. 4; No. 1, pp. 307-320.

Jarrett et al., "Use of the LigaSure™ Vessel Sealing System for Peri-Hilar Vessels in Laparoscopic Nephrectomy" Sales/Product Literature 2000.

Johnson et al., "Evaluation of a Bipolar Electrothermal Vessel Sealing Device in Hemorrhoidectomy" Sales/Product Literature, Jan. 2004.

Johnson, "Evaluation of the LigaSure™ Vessel Sealing System in Hemorrhoidectormy" American College Of Surgeons (ACS) Clinic La Congress Poster (2000).

Johnson, "Use of the LigaSure™ Vessel Sealing System in Bloodless Hemorrhoidectomy" Innovations That Work, Mar. 2000.

Joseph G. Andriole M.D. et al., "Biopsy Needle Characteristics Assessed in the Laboratory", Radiology 148: 659-662, Sep. 1983.

Joseph Ortenberg, "LigaSure™ System Used in Laparoscopic 1st and 2nd Stage Orchiopexy" Innovations That Work, Nov. 2002.

K. Ogata, Modern Control Engineering, Prentice-Hall, Englewood Cliffs, N.J., 1970.

Kennedy et al., "High-burst-strength, feedback-controlled bipolar vessel sealing" Surgical Endoscopy (1998) 12: 876-878.

Kopans, D.B. et al., (Nov. 1985) "Spring Hookwire Breast Lesion Localizer: Use with Rigid-Compression. Mammographic Systems," Radiology 157(2):537-538.

Koyle et al., "Laparoscopic Palomo Varicocele Ligation in Children and Adolescents" Pediatric Endosurgery & Innovative Techniques, vol. 6, No. 1, 2002.

LigaSure™ Vessel Sealing System, the Seal of Confidence in General , Gynecologic, Urologic, and Laparaoscopic Surgery, Sales/Product Literature, Jan. 2004.

Livraghi et al., (1995) "Saline-enhanced RF Tissue Ablation in the Treatment of Liver Metastases", Radiology, pp. 205-210.

Lyndon B. Johnson Space Center, Houston, Texas, "Compact Directional Microwave Antenna for Localized Heating," NASA Tech Briefs, Mar. 2008.

M. A. Astrahan, "A Localized Current Field Hyperthermia System for Use with 192-Iridium Interstitial Implants" Medical Physics. 9(3), May/Jun. 1982.

Magdy F. Iskander et al., "Design Optimization of Interstitial Antennas", IEEE Transactions on Biomedical Engineering, vol. 36, No. 2, Feb. 1989, pp. 238-246.

McGahan et al., (1995) "Percutaneous Ultrasound-guided Radiofrequency Electrocautery Ablation of Prostate Tissue in Dogs", Acad Radiol, vol. 2, No. 1: pp. 61-65.

McLellan et al., "Vessel Sealing for Hemostasis During Pelvic Surgery" Int'l Federation of Gynecology and Obstetrics Figo World Congress 2000, Washington, DC.

MDTECH product literature (Dec. 1999) "FlexStrand": product description, 1 page.

MDTECH product literature (Mar. 2000) I'D Wire: product description, 1 page.

Medtrex Brochure "The O.R. Pro 300" 1 page, Sep. 1998.

Michael Choti, "Abdominoperineal Resection with the LigaSure™ Vessel Sealing System and LigaSure™ Atlas 20 cm Open Instrument" Innovations That Work, Jun. 2003.

Muller et al., "Extended Left Hemicolectomy Using the LigaSure™ Vessel Sealing System" Innovations That Work. LJ, Sep. 1999.

Murakami, R. et al., (1995). "Treatment of Hepatocellular Carcinoma: Value of Percutaneous Microwave Coagulation," American Journal of Radiology (AJR) 164:1159-1164.

Ni Wei et al., "A Signal Processing Method for the Coriolis Mass Flowmeter Based on a Normalized . . . " Journal of Applied Sciences•Yingyong Kexue Xuebao, Shangha CN, vol. 23, No. 2:(Mar. 2005); pp. 160-184.

Ogden, "Goertzel Alternative to the Fourier Transform" Jun. 1993 pp. 485-487 Electronics World; Reed Business Publishing, Sutton, Surrey, BG, vol. 99, No. 9, 1687.

Olsson M.D. et al., "Radical Cystectomy in Females" Current Surgical Techniques in Urology, vol. 14, Issue 3, 2001.
Organ, L W., "Electrophysiologic Principles of Radiofrequency Lesion Making" Appl. Neurophysiol, vol. 39: pp. 69-76 (1976/77).
P.R. Stauffer et al., "Interstitial Heating Technologies", Thermoradiotheray and Thermochemotherapy (1995) vol. I, Biology, Physiology, Physics, pp. 279-320.
Palazzo et al., "Randomized clinical trial of LigaSure™ versus open haemorrhoidectomy" British Journal of Surgery 2002,89,154-157
"Innovations in Electrosurgery" Sales/Product Literature; Dec. 31, 2000.
Paul G. Horgan, "A Novel Technique for Parenchymal Division During Hepatectomy" The American Journal of Surgery, vol. 181, No. 3, Apr. 2001, pp. 236-237.
Peterson et al., "Comparison of Healing Process Following Ligation with Sutures and Bipolar Vessel Sealing" Surgical Technology International (2001).
R. Gennari et al., (Jun. 2000) "Use of Technetium-99m-Labeled Colloid Albumin for Preoperative and Intraoperative Localization of Non palpable Breast Lesions," American College of Surgeons. 190(6):692-699.
Valleylab Brochure, "Reducing Needlestick Injuries in the Operating Room" 1 page, Mar. 2001.
Reidenbach, (1995) "First Experimental Results with Special Applicators for High-Frequency Interstitial Thermotherapy", Society Minimally Invasive Therapy, 4(Suppl 1):40 (Abstr).
Richard Wolf Medical Instruments Corp. Brochure, "Kleppinger Bipolar Forceps & Bipolar Generator" 3 pages, Jan. 1989.
Rothenberg et al., "Use of the LigaSure™ Vessel Sealing System in Minimally Invasive Surgery in Children" Int'l Pediatric Endosurgery Group (I Peg) 2000.
Sayfan et al., "Sutureless Closed Hemorrhoidectomy: A New Technique" Annals of Surgery, vol. 234, No. 1, Jul. 2001, pp. 21-24.
Sengupta et al., "Use of a Computer-Controlled Bipolar Diathermy System in Radical Prostatectomies and Other Open Urological Surgery" ANZ Journal of Surgery (2001) 71.9 pp. 538-540.
Sigel et al., "The Mechanism of Blood Vessel Closure by High Frequency Electrocoagulation" Surgery Gynecology & Obstetrics, Oct. 1965 pp. 823-831.
Solbiati et al., (2001) "Percutaneous Radio-frequency Ablation of Hepatic Metastases from Colorectal Cancer: Long-term Results in 117 Patients", Radiology, vol. 221, pp. 159-166.
Strasberg et al., "Use of a Bipolar Vassel-Sealing Device for Parenchymal Transection During Liver Surgery" Journal of Gastrointestinal Surgery, vol. 6, No. 4, Jul./Aug. 2002 pp. 569-574.
Stuart W. Young, Nuclear Magnetic Resonance Imaging—Basic Principles, Raven Press, New York, 1984.
Sugita et al., "Bipolar Coagulator with Automatic Thermocontrol" J. Neurosurg., vol. 41, Dec. 1944, pp. 777-779.
Sylvain Labonte et al., "Monopole Antennas for Microwave Catheter Ablation", IEEE Trans. on Microwave Theory and Techniques, vol. 44, No. 10, pp. 1832-1840, Oct. 1995.
T. Matsukawa et al., "Percutaneous Microwave Coagulation Therapy in Liver Tumors", Acta Radiologica, vol. 38, pp. 410-415, 1997.
T. Seki et al., (1994) "Ultrasonically Guided Percutaneous Microwave Coagulation Therapy for Small Hepatocellular Carcinoma," Cancer 74(3):817.825.
Urologix, Inc.-Medical Professionals: Targis™ Technology (Date Unknown). "Overcoming the Challenge" located at: <http://www.urologix.com!medicaUtechnology.html > last visited on Apr. 27, 2001, 3 pages.
Urrutia et al., (1988). "Retractable-Barb Needle for Breast Lesion Localization: Use in 60 Cases," Radiology 169(3):845-847.
Valleylab Brochure, "Valleylab Electroshield Monitoring System" 2 pages, Nov. 1995.
ValleyLab Brochure, "Electosurgery: A Historical Overview", Innovations in Electrosurgery, 1999.
Vallfors et al., "Automatically Controlled Bipolar Electrocoagulation-'COA-COMP" Neurosurgical Review 7:2-3 (1984) pp. 187-190.
W. Scott Helton, "LigaSureTM Vessel Sealing System: Revolutionary Hemostasis Product for General Surgery" Sales/Product Literature 1999.
Wald et al., "Accidental Burns", JAMA, Aug. 16, 1971, vol. 217, No. 7, pp. 916-921.
Walt Boyles, "Instrumentation Reference Book", 2002, Butterworth-Heinemann, pp. 262-264.
European Search Report EP 98300964.8 dated Dec. 13, 2000.
European Search Report EP 98944778 dated Nov. 7, 2000.
European Search Report EP 98958575.7 dated Oct. 29, 2002.
European Search Report EP 03721482 dated Feb. 6, 2006.
European Search Report EP 04009964 dated Jul. 28, 2004.
European Search Report EP 04013772 dated Apr. 11, 2005.
European Search Report EP 04015980 dated Nov. 3, 2004.
European Search Report EP 04015981.6 dated Oct. 25, 2004.
European Search Report EP 04027314 dated Mar. 31, 2005.
European Search Report EP 04027479 dated Mar. 17, 2005.
European Search Report EP 04027705 dated Feb. 10, 2005.
European Search Report EP 04710258 dated Oct. 15, 2004.
European Search Report EP 04752343.6 dated Jul. 31, 2007.
European Search Report EP 04778192.7 dated Jul. 1, 2009.
European Search Report EP 05002027.0 dated May 12, 2005.
European Search Report EP 05002769.7 dated Jun. 19, 2006.
European Search Report EP 05013463.4 dated Oct. 7, 2005.
European Search Report EP 05013895 dated Oct. 21, 2005.
European Search Report EP 05014156.3 dated Jan. 4, 2006.
European Search Report EP 05016399 dated Jan. 13, 2006.
European Search Report EP 05017281 dated Nov. 24, 2005.
European Search Report EP 05019130.3 dated Oct. 27, 2005.
European Search Report EP 05019882 dated Feb. 16, 2006.
European Search Report EP 05020665.5 dated Feb. 27, 2006.
European Search Report EP 05020666.3 dated Feb. 27, 2006.
European Search Report EP 05021025.1 dated Mar. 13, 2006.
European Search Report EP 05021197.8 dated Feb. 20, 2006.
European Search Report EP 05021777 dated Feb. 23, 2006.
European Search Report EP 05021779.3 dated Feb. 2, 2006.
European Search Report EP 05021780.1 dated Feb. 23, 2006.
European Search Report EP 05021935 dated Jan. 27, 2006.
European Search Report EP 05021936.9 dated Feb. 6, 2006.
European Search Report EP 05021937.7 dated Jan. 23, 2006.
European Search Report EP 05021939 dated Jan. 27, 2006.
European Search Report EP 05021944.3 dated Jan. 25, 2006.
European Search Report EP 05022350.2 dated Jan. 30, 2006.
European Search Report EP 05023017.6 dated Feb. 24, 2006.
European Search Report EP 05025423.4 dated Jan. 19, 2007.
European Search Report EP 05025424 dated Jan. 30, 2007.
European Search Report EP 05810523 dated Jan. 29, 2009.
European Search Report EP 06000708.5 dated May 15, 2006.
European Search Report EP 06002279.5 dated Mar. 30, 2006.
European Search Report EP 06005185.1 dated May 10, 2006.
European Search Report EP 06005540 dated Sep. 24, 2007.
European Search Report EP 06006717.0 dated Aug. 11, 2006.
European Search Report EP 06006961 dated Oct. 22, 2007.
European Search Report EP 06006963 dated Jul. 25, 2006.
European Search Report EP 06008779.8 dated Jul. 13, 2006.
European Search Report EP 06009435 dated Jul. 13, 2006.
European Search Report EP 06010499.9 dated Jan. 29, 2008.
European Search Report EP 06014461.5 dated Oct. 31, 2006.
European Search Report EP 06018206.0 dated Oct. 20, 2006.
European Search Report EP 06019768 dated Jan. 17, 2007.
European Search Report EP 06020574.7 dated Oct. 2, 2007.
European Search Report EP 06020583.8 dated Feb. 7, 2007.
European Search Report EP 06020584.6 dated Feb. 1, 2007.
European Search Report EP 06020756.0 dated Feb. 16, 2007.
European Search Report EP 06022028.2 dated Feb. 13, 2007.
European Search Report EP 06023756.7 dated Feb. 21, 2008.
European Search Report EP 06024122.1 dated Apr. 16, 2007.
European Search Report EP 06024123.9 dated Mar. 6, 2007.
European Search Report EP 06025700.3 dated Apr. 12, 2007.
European Search Report EP 07000885.9 dated May 15, 2007.
European Search Report EP 07001480.8 dated Apr. 19, 2007.
European Search Report EP 07001481.6 dated May 2, 2007.
European Search Report EP 07001485.7 dated May 23, 2007.
European Search Report EP 07001488.1 dated Jun. 5, 2007.
European Search Report EP 07001489.9 dated Dec. 20, 2007.
European Search Report EP 07001491 dated Jun. 6, 2007.

European Search Report EP 07001527.6 dated May 18, 2007.
European Search Report EP 07007783.9 dated Aug. 14, 2007.
European Search Report EP 07008207.8 dated Sep. 13, 2007.
European Search Report EP 07009026.1 dated Oct. 8, 2007.
European Search Report EP 07009028 dated Jul. 16, 2007.
European Search Report EP 07009029.5 dated Jul. 20, 2007.
European Search Report EP 07009321.6 dated Aug. 28, 2007.
European Search Report EP 07009322.4 dated Jan. 14, 2008.
European Search Report EP 07010672.9 dated Oct. 16, 2007.
European Search Report EP 07010673.7 dated Oct. 5, 2007.
European Search Report EP 07013779.9 dated Oct. 26, 2007.
European Search Report EP 07015191.5 dated Jan. 23, 2007.
European Search Report EP 07015601.3 dated Jan. 4, 2007.
European Search Report EP 07015602.1 dated Dec. 20, 2007.
European Search Report EP 07018375.1 dated Jan. 8, 2008.
European Search Report EP 07018821 dated Jan. 14, 2008.
European Search Report EP 07019173.9 dated Feb. 12, 2008.
European Search Report EP 07019174.7 dated Jan. 29, 2008.
European Search Report EP 07019178.8 dated Feb. 12, 2008.
European Search Report EP 07020283.3 dated Feb. 5, 2008.
European Search Report EP 07253835.8 dated Dec. 20, 2007.
European Search Report EP 08001019 dated Sep. 23, 2008.
European Search Report EP 08004975 dated Jul. 24, 2008.
European Search Report EP 08006731.7 dated Jul. 29, 2008.
European Search Report EP 08006733 dated Jul. 7, 2008.
European Search Report EP 08006734.1 dated Aug. 18, 2008.
European Search Report EP 08006735.8 dated Jan. 8, 2009.
European Search Report EP 08011282 dated Aug. 14, 2009.
European Search Report EP 08011705 dated Aug. 20, 2009.
European Search Report EP 08012829.1 dated Oct. 29, 2008.
European Search Report EP 08015842 dated Dec. 5, 2008.
European Search Report EP 08019920.1 dated Mar. 27, 2009.
European Search Report EP 08169973.8 dated Apr. 6, 2009.
European Search Report EP 09156861.8 dated Aug. 4, 2009.
European Search Report EP 09161502.1 dated Sep. 2, 2009.
European Search Report EP 09166708 dated Oct. 15, 2009.
International Search Report PCT/US98/18640 dated Jan. 29, 1998.
International Search Report PCT/US98/23950 dated Jan. 14, 1998.
International Search Report PCT/US99/24869 dated Feb. 11, 2000.
International Search Report PCT/US01/11218 dated Aug. 14, 2001.
International Search Report PCT/US01/11224 dated Nov. 13, 2001.
International Search Report PCT/US01/11340 dated Aug. 16, 2001.
International Search Report PCT/US01/11420 dated Oct. 16, 2001.
International Search Report PCT/US02/01890 dated Jul. 25, 2002.
International Search Report PCT/US02/11100 dated Jul. 16, 2002.
International Search Report PCT/US03/09483 dated Aug. 13, 2003.
International Search Report PCT/US03/22900 dated Dec. 2, 2003.
International Search Report PCT/US03/37110 dated Jul. 25, 2005.
International Search Report PCT/US03/37111 dated Jul. 28, 2004.
International Search Report PCT/US03/37310 dated Aug. 13, 2004.
International Search Report PCT/US04/04685 dated Aug. 27, 2004.
International Search Report PCT/US04/13273 dated Dec. 15, 2004.
International Search Report PCT/US04/15311 dated Jan. 12, 2004.
International Search Report PCT/US05/36168 dated Aug. 28, 2006.
International Search Report PCT/US08/052460 dated Apr. 24, 2008.
International Search Report PCT/US09/31658 dated Mar. 11, 2009.

* cited by examiner

FEEDPOINT OPTIMIZATION FOR MICROWAVE ABLATION DIPOLE ANTENNA WITH INTEGRATED TIP

BACKGROUND

1. Technical Field

The present disclosure relates generally to microwave ablation procedures that utilize microwave surgical devices having a microwave antenna which may be inserted directly into tissue for diagnosis and treatment of diseases. More particularly, the present disclosure is directed to an integrated matching network in the feedpoint structure of a microwave dipole antenna.

2. Background of Related Art

In the treatment of diseases such as cancer, certain types of cancer cells have been found to denature at elevated temperatures (which are slightly lower than temperatures normally injurious to healthy cells.) These types of treatments, known generally as hyperthermia therapy, typically utilize electromagnetic radiation to heat diseased cells to temperatures above 41° C., while maintaining adjacent healthy cells at lower temperatures where irreversible cell destruction will not occur. Other procedures utilizing electromagnetic radiation to heat tissue also include ablation and coagulation of the tissue. Such microwave ablation procedures, e.g., such as those performed for menorrhagia, are typically done to ablate and coagulate the targeted tissue to denature or kill the tissue. Many procedures and types of devices utilizing electromagnetic radiation therapy are known in the art. Such microwave therapy is typically used in the treatment of tissue and organs such as the prostate, heart, liver, lung, kidney, and breast.

One non-invasive procedure generally involves the treatment of tissue (e.g., a tumor) underlying the skin via the use of microwave energy. The microwave energy is able to non-invasively penetrate the skin to reach the underlying tissue. However, this non-invasive procedure may result in the unwanted heating of healthy tissue. Thus, the non-invasive use of microwave energy requires a great deal of control.

Presently, there are several types of microwave probes in use, e.g., monopole, dipole, and helical. One type is a monopole antenna probe, which consists of a single, elongated microwave conductor exposed at the end of the probe. The probe is typically surrounded by a dielectric sleeve. The second type of microwave probe commonly used is a dipole antenna, which consists of a coaxial construction having an inner conductor and an outer conductor with a dielectric junction separating a portion of the inner conductor. The inner conductor may be coupled to a portion corresponding to a first dipole radiating portion, and a portion of the outer conductor may be coupled to a second dipole radiating portion. The dipole radiating portions may be configured such that one radiating portion is located proximally of the dielectric junction, and the other portion is located distally of the dielectric junction. In the monopole and dipole antenna probe, microwave energy generally radiates perpendicularly from the axis of the conductor.

The typical microwave antenna has a long, thin inner conductor that extends along the axis of the probe and is surrounded by a dielectric material and is further surrounded by an outer conductor around the dielectric material such that the outer conductor also extends along the axis of the probe. In another variation of the probe that provides for effective outward radiation of energy or heating, a portion or portions of the outer conductor can be selectively removed. This type of construction is typically referred to as a "leaky waveguide" or "leaky coaxial" antenna. Another variation on the microwave probe involves having the tip formed in a uniform spiral pattern, such as a helix, to provide the necessary configuration for effective radiation. This variation can be used to direct energy in a particular direction, e.g., perpendicular to the axis, in a forward direction (i.e., towards the distal end of the antenna), or combinations thereof.

Invasive procedures and devices have been developed in which a microwave antenna probe may be either inserted directly into a point of treatment via a normal body orifice or percutaneously inserted. Such invasive procedures and devices potentially provide better temperature control of the tissue being treated. Because of the small difference between the temperature required for denaturing malignant cells and the temperature injurious to healthy cells, a known heating pattern and predictable temperature control is important so that heating is confined to the tissue to be treated. For instance, hyperthermia treatment at the threshold temperature of about 41.5° C. generally has little effect on most malignant growth of cells. However, at slightly elevated temperatures above the approximate range of 43° C. to 45° C., thermal damage to most types of normal cells is routinely observed. Accordingly, great care must be taken not to exceed these temperatures in healthy tissue.

In the case of tissue ablation, a high frequency electrical current in the range of about 500 mHz to about 10 gHz is applied to a targeted tissue site to create an ablation volume, which may have a particular size and shape. Ablation volume is correlated to antenna design, antenna performance, antenna impedance and tissue impedance. The particular type of tissue ablation procedure may dictate a particular ablation volume in order to achieve a desired surgical outcome. By way of example, and without limitation, a spinal ablation procedure may call for a longer, narrower ablation volume, whereas in a prostate ablation procedure, a more spherical ablation volume may be required.

In microwave ablation devices, when microwave energy is delivered to an antenna by a feed line, the impedance of the antenna and feed line must match exactly for maximum energy transfer from the feed line to the antenna to be possible. The impedance of the antenna varies based on many factors including the antenna's natural resonance at the frequency being transmitted and the size of the conductors used to construct the antenna. When an antenna and feed line do not have matching impedances, some of the electrical energy cannot be transferred from the feed line to the antenna. Energy not transferred to the antenna is reflected back towards the transmitter. It is the interaction of these reflected waves with forward waves which causes standing wave patterns. Reflected power has three main implications: microwave frequency (MW) energy losses increase, distortion in the microwave generator due to reflected power from load and damage to the transmitter can occur.

The voltage standing wave ratio (VSWR) is a measure of how well a load is impedance-matched to a source. The value of VSWR is always expressed as a ratio with 1 in the denominator (2:1, 3:1, 10:1, etc.). It is a scalar measurement only (no angle), so although they reflect waves oppositely, a short circuit and an open circuit have the same VSWR value (infinity:1). A perfect impedance match corresponds to a VSWR of 1 (1:1).

Figure 4:
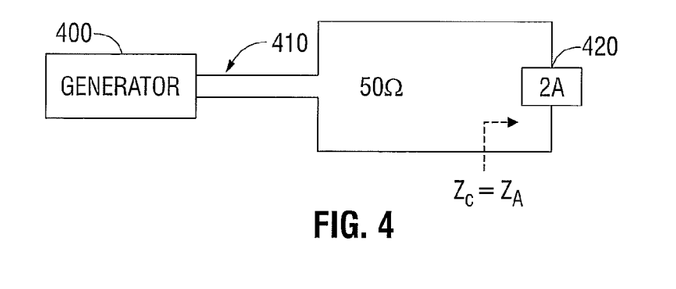
FIG. 4 shows a transmission line structure used model a radiating portion of a dipole antenna without an integrated matching network.

In regular antennas used during microwave ablation procedures there is not a maximum transfer of energy. For example, the regular dipole antenna without an integrated matching network can be modeled using the transmission line structure shown in FIG. 4. As shown in FIG. 4, the antenna 420 is coupled to a generator 400 via a coax cable 410 that has an impedance ($Z_c$) of 50Ω. In the presence of a half wave ($\lambda/2$)

dipole antenna, the impedance ($Z_A$) of the antenna 420 is 73Ω according to dipole antenna theory. This results in a VSWR of 1.46 and, as such, some of the energy is not transferred to the antenna.

SUMMARY

The present disclosure provides a microwave ablation system. The microwave ablation system includes a generator operable to output energy, an antenna coupled to the generator via a coaxial cable. The antenna is operable to deliver energy to tissue and includes a proximal radiating section and a distal radiating section. The antenna also includes a feedpoint section defined by the portion of the distal radiating section that underlaps the proximal radiating section.

In another embodiment of the present disclosure, an antenna for use in a microwave ablation system is provided. The antenna is operable to deliver energy to tissue and includes a proximal radiating section and a distal radiating section. The antenna also includes a feedpoint section defined by the portion of the distal radiating section that underlaps the proximal radiating section.

In other embodiments, the proximal radiating section is a semi rigid coaxial cable and/or the distal radiating section is a hypotube.

In yet another embodiment, the distal radiating section is filled with a dielectric material having a first permittivity constant. The feedpoint section may also be filled with a dielectric material having the first permittivity constant.

In other embodiments, the feedpoint section is filled with a dielectric material having a second permittivity constant different from the first permittivity constant.

In other embodiments, an impedance of the feedpoint section is based on the first permittivity constant, an inner diameter of the proximal radiating section and the outer diameter of the distal radiating section.

BRIEF DESCRIPTION OF THE DRAWINGS

The above and other aspects, features, and advantages of the present disclosure will become more apparent in light of the following detailed description when taken in conjunction with the accompanying drawings in which.

DETAILED DESCRIPTION

Particular embodiments of the present disclosure are described hereinbelow with reference to the accompanying drawings; however, it is to be understood that the disclosed embodiments are merely examples of the disclosure and may be embodied in various forms. Well-known functions or constructions are not described in detail to avoid obscuring the present disclosure in unnecessary detail. Therefore, specific structural and functional details disclosed herein are not to be interpreted as limiting, but merely as a basis for the claims and as a representative basis for teaching one skilled in the art to variously employ the present disclosure in virtually any appropriately detailed structure. Like reference numerals may refer to similar or identical elements throughout the description of the Fig.s. As used herein, the term "distal" refers to that portion of the instrument, or component thereof which is closer to the patient while the term "proximal" refers to that portion of the instrument or component thereof which is further from the patient.

Electromagnetic energy is generally classified by increasing energy or decreasing wavelength into radio waves, microwaves, infrared, visible light, ultraviolet, X-rays and gamma-rays. As used herein, the term "microwave" generally refers to electromagnetic waves in the frequency range of 300 megahertz (MHz) ($3 \times 10^8$ cycles/second) to 300 gigahertz (GHz) ($3 \times 10^{11}$ cycles/second). As used herein, the term "RF" generally refers to electromagnetic waves having a lower frequency than microwaves. The phrase "ablation procedure" generally refers to any ablation procedure, such as RF or microwave ablation or microwave ablation assisted resection. The phrase "transmission line" generally refers to any transmission medium that can be used for the propagation of signals from one point to another.

Figure 1:
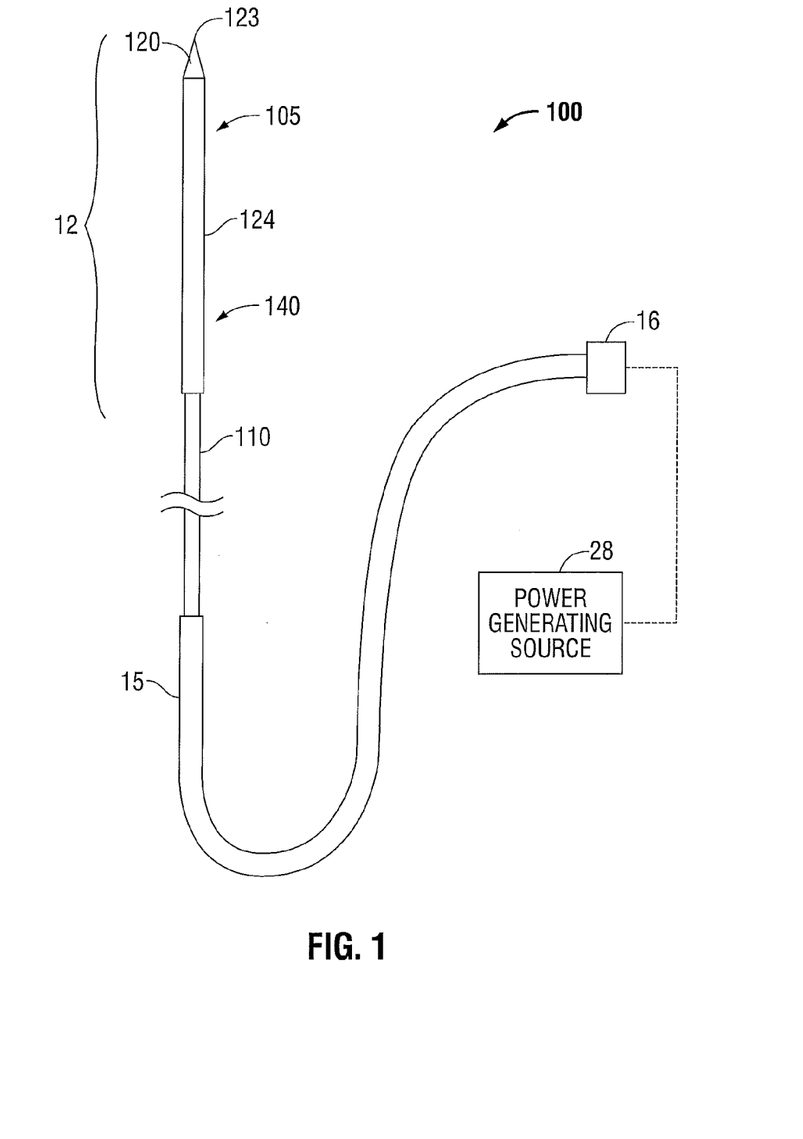
FIG. 1 shows a representative diagram of a variation of a microwave antenna assembly in accordance with an embodiment of the present disclosure.

FIG. 1 shows a microwave antenna assembly 100 in accordance with one embodiment of the present disclosure. Antenna assembly 100 includes a radiating portion 12 that is connected by feed line 110 (or shaft) via cable 15 to connector 16, which may further connect the assembly 10 to a power generating source 28, e.g., a microwave or RF electrosurgical generator. Assembly 100, as shown, is a dipole microwave antenna assembly, but other antenna assemblies, e.g., monopole antenna assemblies, may also utilize the principles set forth herein. Distal radiating section 105 of radiating portion 12 includes a tapered end 120 which terminates at a tip 123 to allow for insertion into tissue with minimal resistance. It is to be understood, however, that tapered end 120 may include other shapes, such as without limitation, a tip 123 that is rounded, flat, square, hexagonal, cylindroconical or any other polygonal shape.

An outer jacket 124 is disposed about the outer cylindrical surface of antenna assembly 100, e.g., the distal radiating section 105 and proximal radiating section 140. Outer jacket 124 may be formed from any suitable material, including without limitation polymeric or ceramic materials. In some embodiments, outer jacket 124 is formed from PTFE. Outer jacket 124 may be applied to antenna assembly 100 by any suitable manner, including without limitation, heat shrinking.

Figure 2:
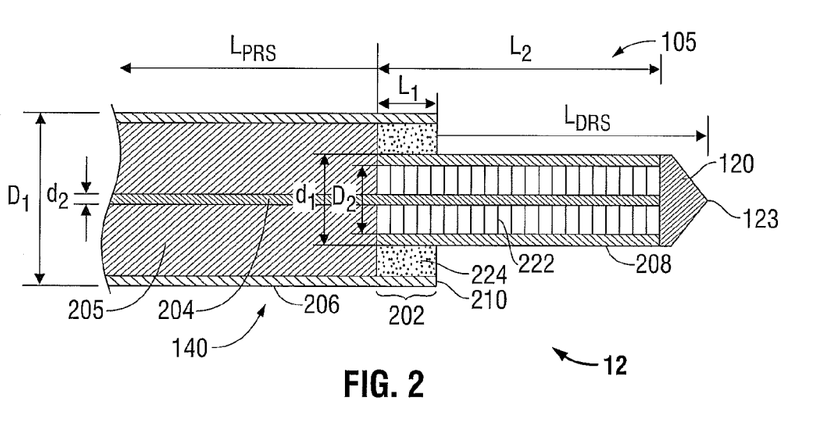
FIG. 2 shows a cross-sectional view of a radiating portion of a microwave antenna assembly in accordance with an embodiment of the present disclosure.

FIG. 2 shows a cross sectional view of radiating portion 12 of the antenna assembly 100. In an embodiment of the present disclosure, a matching network is integrated into the radiating portion 12 at the feedpoint section 202 by underlapping the distal radiating section 105 into proximal radiating section 140 that extends distally from the feed line 110. The inner conductor 204 is extended to distal end of the distal radiating section 105 and electrically coupled to the distal radiating section 105 thereby creating a short circuit.

As shown in FIG. 2, the proximal radiating section 140 is a semi rigid coaxial cable with an outer conductor 206 and an inner conductor 204 extending through the proximal radiating section 140 into the distal radiating section 105. Proximal radiating section is filled with a dielectric material 205 having a permittivity $\in_C$ along the length $L_{PRS}$ that results in a characteristic impedance ($Z_C$) for the proximal radiating section of 50Ω. The inner portion of the outer conductor 206 of the proximal radiating section 140 has a diameter $D_1$ as shown in FIG. 2. The inner conductor extending through the proximal radiating section 140 has a diameter $d_2$.

The distal radiating section 105 includes a TW hypotube 208 having a length $L_2$ with an outer diameter $d_1$ and an inner diameter of $D_2$. The length $L_{DRS}$ of the distal radiating section 105 extends from end 210 of the underlapping of the distal radiating section 105 and proximal radiating section 140 to tip 123. Hypotube 208 is filled with a dielectric material 222 having a permittivity $\in_2$.

Feedpoint section 202 includes the underlapping of the distal radiating section 105 and the proximal radiating section 140. The underlapping has a length $L_1$ which can be varied to optimize the feedpoint for maximum transfer of energy. Along length $L_1$, the feedpoint is filled with a dielectric material 224 having a permittivity $\in_1$. Dielectric materials 222 and 224 may have the same permittivity constant or different permittivity constants.

The underlap forms a first coaxial line of length $L_1$ with a characteristic impedance of $Z_{O1}$ which depends on the radial dimensions $d_1$ and $D_1$ and dielectric $\in_1$. $Z_{O1}$ can be calculated using the equation:

$$Z_{O1} = \frac{138}{\sqrt{\varepsilon_1}} \text{Log}_{10}\left(\frac{D_1}{d_1}\right)$$

The wavelength ($\lambda 1$) inside the first coaxial line can be calculated using the equation:

$$\lambda_1 = \frac{c}{f\sqrt{\varepsilon_1}},$$

where f equals frequency and c equals the speed of light.

The inner conductor 204 and the distal radiating section 105 forms a second coaxial line terminating in a short circuit having a length L2 and a characteristic impedance $Z_{O2}$. $Z_{O2}$ can be calculated using the equation:

$$Z_{O2} = \frac{138}{\sqrt{\varepsilon_2}} \text{Log}_{10}\left(\frac{D_2}{d_2}\right)$$

Figure 3:
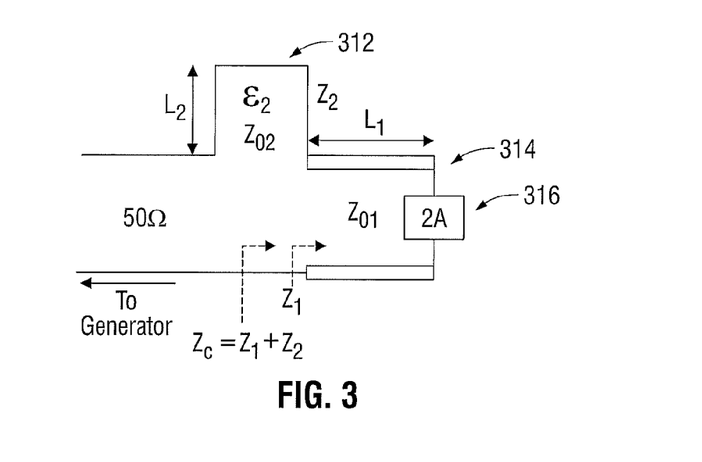
FIG. 3 shows a transmission line structure used to model a radiating portion of a microwave antenna assembly in accordance with an embodiment of the present disclosure.

The wavelength ($\lambda 2$) inside the first coaxial line can be calculated using the equation:

$$\lambda_2 = \frac{c}{f\sqrt{\varepsilon_2}},$$

where f equals frequency and c equals the speed of light,

FIG. 3 shows a transmission line structure 310 that can be used to model the radiating portion 12 according to an embodiment of the present disclosure. In the model, the 50Ω coaxial cable or feed line is in series with a shorted stub 312 having a length $L_2$ and an impedance $Z_{O2}$ and a piece of line 314 having a length $L_1$ and an impedance $Z_{O1}$ all terminating on an antenna load 316 having an impedance $Z_A$. In the matching network, the sum of $Z_1$ and $Z_2$ should equal the 50Ω coaxial cable in order to obtain a VSWR equal to 1 for maximum energy transfer. This can be accomplished by varying the lengths $L_1$ and $L_2$ and the dielectric permittivity constants $\in_1$ and $\in_2$ so that the sum of $Z_1$ and $Z_2$ equals or is close to the 50Ω coaxial cable.

According to basic transmission line theory, $L_1$ can be selected so that $Z_1$ will have a resistance of 50Ω and a reactance of $X_1$. Therefore, $Z_1$ would equal $50\,\Omega + jX_1$. $L_2$ can also be selected so that $Z_2 = -jX_1$. Therefore, the sum of $Z_1$ and $Z_2$ would equal 50Ω. In an example according to an embodiment of the present disclosure, a 0.047" coaxial cable can be used for proximal radiating section 140 having an inner conductor diameter (d2) of 0.011" and an outer conductor inner diameter ($D_1$) of 0.037". A 22 gauge TW hypotube can be used for the distal radiating section 105 having an inner diameter ($D_2$) of 0.020" and outer diameter ($d_1$) of 0.028". Teflon® can be used as dielectric material 224 having a permittivity ($\in_1$) of 2.1. Accordingly, $Z_{O1}$ would equal 11.5Ω. If $L_1$ was moved 0.018λ towards the generator, than the new normalized impedance ($Z_{N1}$) would be equal to 4.35−j2.9 and $Z_1 = Z_{N1} * Z_{O1} = 50\Omega - j33.5$. At 915 MHz, $\lambda_1 = 0.226$ m and $L_1 = 0.018\lambda_1 = 4$ mm.

If Teflon® was also used as dielectric material 222, impedance ($Z_{O2}$) would be 24.7Ω. In order to obtain $Z_2 = j33.5\Omega$, $Z_{N2}$ would be 1.36Ω and $L_2$ would be 0.148λ which equals 3.3 cm. Since the antenna is a λ/2 dipole antenna that is typically 3.8 cm long at 915 MHz, the $L_{DRS} = 1.9$ cm. The distal radiating section 105 has a tapered end 120 with a sharp tip 123 that is typically 4-5 mm long. Assuming a length of the tip as 4 mm and a length of 4 mm for $L_1$, the maximum length for $L_2$ is limited to 1.9 cm. Accordingly, the length of 3.3 cm needed to provide a perfect match with Teflon® is too long. If $L_2$ was 1.9 cm, $L_2$ would be 0.84λ resulting in a reactance of 0.59 which would results in $Z_2$ being j14.6Ω. As such, with Teflon® being used as dielectric material 222 and 224, the sum of $Z_1$ and $Z_2$ would be 50Ω−j18.9 resulting in a VSWR of 1.46 which would be the same as an antenna without a matching network.

However, if alumina was used for dielectric material 222, ($\in_2 = 9$), λ2 would be 0.1093 m and $Z_{O2}$ would equal 11.94Ω. In order for $Z_{N2}$ to equal 2.81, $L_2$ would have to equal 2.1 cm which would still be too long as described above. Accordingly, if $L_2$ remains at 1.9 cm which equals 0.174λ, then the reactance would equal 1.93 and $Z_2$ would equal j23. The sum of $Z_1$ and $Z_2$ would be 50Ω−j10.5 which would result in a VSWR of 1.23. Therefore, the use of a combination of Teflon® and alumina would result in a better impedance matching and more energy would be transferred than an antenna without a matching network.

It should be noted that different materials could be used than the ones listed in the examples above. By varying the dielectric materials used, the types of coaxial cable and hypotubes and the lengths $L_1$ and $L_2$, a better impedance match may be obtained. Other dielectric materials that may be used include, but are not limited to, titanium dioxide, which has a permittivity ranging from 10-40, or other ceramic materials having a similar permittivity. Low density Teflon® may also be used instead of regular Teflon®.

The described embodiments of the present disclosure are intended to be illustrative rather than restrictive, and are not intended to represent every embodiment of the present disclosure. Various modifications and variations can be made without departing from the spirit or scope of the disclosure as set forth in the following claims both literally and in equivalents recognized in law.

What is claimed is:

1. A microwave ablation system, comprising:
   a generator operable to output energy; and
   an antenna coupled to the generator via a coaxial cable, the antenna operable to deliver energy to tissue, said antenna comprising:
   a proximal radiating section;
   a distal radiating section; and a feedpoint section defined by a portion of the distal radiating section that underlaps the proximal radiating section,
wherein the portion of the distal radiating section that underlaps the proximal radiating section is variable along a longitudinal length of the antenna.

2. The microwave ablation system according to claim 1, wherein the proximal radiating section is a semi rigid coaxial cable.

3. The microwave ablation system according to claim 1, wherein the distal radiating section is a hypotube.

4. The microwave ablation system according to claim 1, wherein the distal radiating section is filled with a dielectric material having a first permittivity constant.

5. The microwave ablation system according to claim 4, wherein the feedpoint section is filled with a dielectric material having the first permittivity constant.

6. The microwave ablation system according to claim 5, wherein an impedance of the feedpoint section is based on the first permittivity constant, an inner diameter of the proximal radiating section and an outer diameter of the distal radiating section.

7. The microwave ablation system according to claim 4, wherein the feedpoint section is filled with a dielectric material having a second permittivity constant different from the first permittivity constant.

8. An antenna for use in a microwave ablation system, comprising:
a proximal radiating section;
a distal radiating section; and
a feedpoint section defined by a portion of the distal radiating section that underlaps the proximal radiating section,
wherein the portion of the distal radiating section that underlaps the proximal radiating section is variable along a longitudinal length of the antenna.

9. The antenna according to claim 8, wherein the proximal radiating section is a semi rigid coaxial cable.

10. The antenna according to claim 8, wherein the distal radiating section is a hypotube.

11. The antenna according to claim 8, wherein the distal radiating section is filled with a dielectric material having a first permittivity constant.

12. The antenna according to claim 11, wherein the feedpoint section is filled with a dielectric material having the first permittivity constant.

13. The antenna according to claim 12, wherein an impedance of the feedpoint section is based on the first permittivity constant, an inner diameter of the proximal radiating section and an outer diameter of the distal radiating section.

14. The antenna according to claim 11, wherein the feedpoint section is filled with a dielectric material having a second permittivity constant different from the first permittivity constant.

* * * * *